US00PP14486P29

(12) United States Plant Patent
Drewlow

(10) Patent No.: US PP14,486 P2
(45) Date of Patent: Jan. 27, 2004

(54) NEW GUINEA IMPATIENS PLANT NAMED 'OVATION SUNCATCHER ORANGE'

(50) Latin Name: *Impatiens hawkeri*
Varietal Denomination: Ovation Suncatcher Orange

(75) Inventor: Lyndon W. Drewlow, Lompoc, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 10/317,305

(22) Filed: Dec. 12, 2002

(51) Int. Cl.[7] ..... A01H 5/00
(52) U.S. Cl. ..... Plt./318
(58) Field of Search ..... Plt./318

*Primary Examiner*—Kent Bell
(74) *Attorney, Agent, or Firm*—C. A. Whealy

(57) ABSTRACT

A new and distinct cultivar of New Guinea Impatiens plant named 'Ovation Suncatcher Orange', characterized by its mounded plant habit; freely branching growth habit; dark and yellow green variegated leaves; freely flowering habit with flowers positioned above or beyond the foliage; large orange red-colored flowers; and tolerance to full sun conditions and low and high temperatures.

1 Drawing Sheet

Botanical classification/cultivar designation: *Impatiens hawkeri* cultivar Ovation Suncatcher Orange.

BACKGROUND OF THE INVENTION

The present Invention relates to a new and distinct cultivar of New Guinea Impatiens plant, botanically known as *Impatiens hawkeri*, and hereinafter referred to by the cultivar name 'Ovation Suncatcher Orange'.

The new Impatiens is a product of a planned breeding program Inventor in Ashtabula, Ohio and Lompoc, Calif. The objective of the breeding program is to develop new freely flowering Impatiens cultivars with interesting flower and foliage colors.

The new Impatiens originated from a cross-pollination made by the Inventor during the winter of 1997 of a proprietary *Impatiens hawkeri* seedling selection designated as code number 97-930-1, not patented, as the female, or seed parent, with the *Impatiens hawkeri* cultivar Encounters, not patented, as the male, or pollen parent. The cultivar Ovation Suncatcher Orange was discovered and selected by the Inventor as a flowering plant within the progeny of the stated cross in controlled environment in Ashtabula, Ohio.

Asexual reproduction of the new cultivar by terminal cuttings taken at Lompoc, Calif., since August, 1998, has shown that the unique features of this new Impatiens are stable and reproduced true to type in successive generations. Plants of the new Impatiens differ from the female parent selection and the cultivar Encounters in plant size and habit, leaf color, and flower size.

SUMMARY OF THE INVENTION

The following traits have been repeatedly observed and are determined to be the unique characteristics of 'Ovation Suncatcher Orange'. These characteristics in combination distinguish 'Ovation Suncatcher Orange' as a new and distinct Impatiens cultivar:

1. Mounded plant habit.
2. Freely branching growth habit, dense and full plants.
3. Dark and yellow green variegated leaves.

4. Freely flowering habit with flowers positioned above or beyond the foliage.
5. Large, orange red-colored flowers.
6. Tolerant to full sun conditions and low and high temperatures.

Plants of the new Impatiens can be compared to plants of the cultivar BFP-605 Orange, disclosed in U.S. Plant Pat. No. 10,078. In side-by-side comparisons conducted in Lompoc, Calif., plants of the new Impatiens differed from plants of the cultivar BFP-605 Orange, in the following characteristics:

1. Plants of the new Impatiens were shorter, denser and more mounded (not as upright) than plants of the cultivar BFP-605 Orange.
2. Plants of the new Impatiens had broader leaves than plants of the cultivar BFP-605 Orange.
3. Plants of the new Impatiens had variegated leaves whereas plants of the cultivar BFP-605 Orange had non-variegated leaves.
4. Plants of the new Impatiens had larger flowers than plants of the cultivar BFP-605 Orange.
5. Plants of the new Impatiens had shorter flower spurs than plants of the cultivar BFP-605 Orange.

Plants of the new Impatiens can also be compared to plants of the cultivar Cameo, disclosed in U.S. Plant Pat. No. 8,316. In side-by-side comparisons conducted in Lompoc, Calif., plants of the new Impatiens differed from plants of the cultivar Cameo, in the following characteristics:

1. Plants of the new Impatiens were shorter and more mounded (not as upright) than plants of the cultivar Cameo.
2. Plants of the new Impatiens had larger flowers than plants of the cultivar Cameo.
3. Flower color of plants of the new Impatiens was orange red whereas flower color of plants of the cultivar Cameo was light red.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Ovation Suncatcher Orange' grown in a container.

DETAILED BOTANICAL DESCRIPTION

The cultivar Ovation Suncatcher Orange has not been observed under all possible environmental conditions. The phenotype may vary somewhat with variations in environment such as temperature and light intensity, without, however, any variance in genotype. The aforementioned photographs and following detailed botanical description describe plants grown in Lompoc, Calif., during the winter, under commercial practice in a fiberglass-covered greenhouse. Plants used in the following description were grown in 15-cm containers for about seven to nine weeks after planting rooted cuttings. During the production period, day temperatures were about 21 to 24° C., night temperatures were about 16 to 18° C., and light levels were about 3,000 to 4,000 foot-candles.

In the following description, color references are made to The Royal Horticultural Society Colour Chart, 1995 Edition, except where general terms of ordinary dictionary significance are used.

Botanical classification: *Impatiens hawkeri* cultivar Ovation Suncatcher Orange.

Commercial classification: New Guinea Impatiens cultivar Ovation Suncatcher Orange.

Parentage:

*Female parent*.—Proprietary *Impatiens hawkeri* seedling selection designated as code number 97-930-1, not patented.

*Male parent*.—*Impatiens hawkeri* cultivar Encounters, not patented.

Propagation:

*Type cutting*.—Terminal cuttings.

*Time to initiate roots*.—Summer: About 10 days at 21° C. Winter: About 12 days at 21° C.

*Time to produce a rooted young plant, summer and winter*.—About 21 days at 21° C.

*Root description*.—Fibrous, white in color.

*Rooting habit*.—Freely branching, dense.

Plant description:

*General appearance*.—Mounded plant habit; numerous large flowers positioned above and beyond the foliage.

*Growth and branching habit*.—Freely branching habit; dense and full plant habit; typically about ten lateral branches develop per plant; pinching, that is, removal of the terminal apices, is usually not required. Vigorous growth habit.

*Plant height*.—About 15 to 20 cm.

*Plant width* (*spread*).—About 30 to 35 cm.

*Lateral branch description*.—Length: About 12 to 15 cm. Diameter: About 8 to 10 mm. Internode length: About 3 to 4 cm. Color: 146B; tinged with 60C.

*Foliage description*.—Arrangement: Alternate or whorled; simple. Length: About 10 to 11 cm. Width: About 3.5 to 4 cm. Shape: Lanceolate to narrowly ovate. Apex: Acuminate. Base: Acute. Margin: Serrulate with ciliation. Texture, upper and lower surfaces: Glabrous, smooth. Venation pattern: Pinnate. Color: Developing foliage, upper surface: 147A. Developing foliage, lower surface: 146B. Fully expanded foliage, upper surface: Towards margins, 147A; center, 153C. Fully expanded foliage, lower surface: Towards margins, 148B; center, 153D. Venation, upper and lower surfaces: 146A. Petiole length: About 8 to 10 mm. Petiole diameter: About 3 mm. Petiole color: 148D, tinged with 63C.

Flower description:

*Flower type and flowering habit*.—Single, large, rounded, flat and orange red-colored flowers. Freely flowering habit, usually about one flower per leaf axil. Flowers positioned above and beyond the foliage and typically face upward or outward. Flowers last about two weeks on the plant depending on environmental conditions. Petals self-cleaning; gynoecium persistent. Flowers not fragrant.

*Flowering season*.—Year-round under greenhouse conditions. In the garden, flowering from spring until fall. Flowering indeterminate and continuous.

*Flower diameter*.—About 7.5 to 8 cm.

*Flower buds*.—Rate of opening: From flower bud to fully open flower, typically about five to seven days depending on temperature. Length: About 2 cm. Diameter: About 1.2 cm. Shape: Ellipsoidal. Color (just before opening): Towards apex, 46A; towards base, 43A.

*Petals*.—Quantity: Single, five per flower, imbricate. Length: About 3.5 cm. Width: About 5 cm. Shape: Roughly cordate. Apex: Emarginate. Base: Acute. Margin: Entire. Texture, upper and lower surfaces: Smooth; satiny. Color: When opening, upper surface: 43A. When opening, lower surface: 40B. Fully opened, upper surface: 43B; color does not fade with development. Fully opened, lower surface: 40B.

*Spur*.—Length: About 5.5 cm. Color: 184C.

*Peduncles*.—Length: About 4.5 cm. Strength: Strong, flexible. Angle: About 45° from vertical. Color: 148D, tinged with 185C.

*Reproductive organs*.—Androecium: Stamen number: Five fused at anthers, filaments free, hooded. Anther length: About 6 mm. Anther shape: Obovate. Anther color: Towards apex, 158A; towards base, 43A. Amount of pollen: Abundant. Pollen color: Close to 155D. Gynoecium: Pistil number: One, five-segmented. Pistil length: About 8 mm. Stigma color: 158A. Style color: Yellow green. Ovary color: 146A.

*Fruit/seed development*.—Fruit and seed development has not been observed.

Disease/pest resistance: Plants of the new Impatiens have not been observed to be resistant to pathogens and pests common to Impatiens.

Light & temperature tolerance: In outdoor nursery trials in Connellsville, Pa., plants of the new Impatiens have been observed to be tolerant to full sun conditions and high temperatures (32 to 38° C.) during the summer. In outdoor nursery trials in Lompoc, Calif., plants of the new Impatiens have been observed to be tolerant to low night temperatures from about 5 to 10° C.

It is claimed:

1. A new and distinct cultivar of New Guinea Impatiens plant named 'Ovation Suncatcher Orange', as illustrated and described.

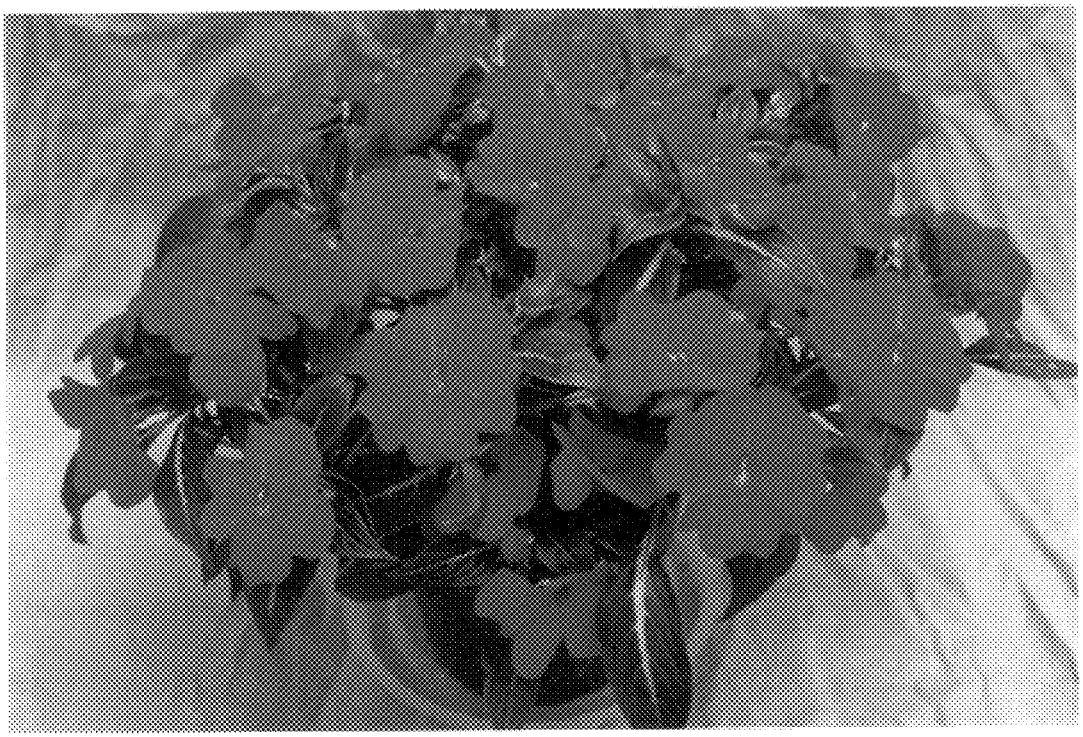

* * * * *